United States Patent [19]

Sakimae et al.

[11] 4,276,381

[45] Jun. 30, 1981

[54] PREPARATION OF IMMOBILIZED ENZYMES OF MICROORGANISMS

[75] Inventors: Akihiro Sakimae, Otake; Hisao Onishi, Hiroshima, both of Japan

[73] Assignee: Mitsubishi Rayon Company, Ltd., Tokyo, Japan

[21] Appl. No.: 60,907

[22] Filed: Jul. 26, 1979

[30] Foreign Application Priority Data

Apr. 9, 1979 [JP] Japan .................................. 54/42725

[51] Int. Cl.³ ...................... C12N 11/12; C12N 11/04
[52] U.S. Cl. .................................... 435/179; 435/180; 435/182
[58] Field of Search ............... 435/174, 177, 180, 179, 435/182

[56] References Cited

U.S. PATENT DOCUMENTS 3,860,490  1/1975  Guttag ................................. 435/182
3,962,038  6/1976  Kawashima et al. ............ 435/182 X

FOREIGN PATENT DOCUMENTS 953414  3/1964  United Kingdom .................... 435/182

*Primary Examiner*—David M. Naff
*Attorney, Agent, or Firm*—Oblon, Fisher, Spivak, McClelland & Maier

[57] ABSTRACT

Immobilized enzymes or microorganisms are prepared by dispersing lumps of ice containing an enzyme or microorganism in an organic solvent having a water-insoluble high-molecular weight substance dissolved therein, and then removing the organic solvent to entrap the ice lumps in the water-insoluble high-molecular weight substance. Deactivation of the enzyme or microorganism by the organic solvent is prevented by the enzyme or microorganism being entrapped in the lumps of ice.

8 Claims, No Drawings

PREPARATION OF IMMOBILIZED ENZYMES OF MICROORGANISMS

BACKGROUND OF THE INVENTION

1. Field of the Invention

The present invention relates to a process for preparing immobilized enzymes or microorganisms. More specifically, the invention is concerned with a process for preparing immobilized enzymes or microorganisms which comprises entrapping enzymes or living microorganisms in a water-insoluble high-molecular weight substance.

2. Description of the Prior Art

Enzymes and microorganisms have recently been extensively used in such fields as the foodstuff industry and the pharmaceutical industry, and have, therefore, acquired renewed importance and interest. According to the conventional prior art processes, the enzymes are dissolved in water and the microorganisms are suspended in water in order to carry out the reaction. Using these methods, however, it is difficult to recover them from the reaction mixture after completion of the reaction. Therefore, the enzymes or microorganisms once used have to be discarded. Because of this, batchwise reaction steps have customarily been employed for reactions using enzymes or microorganisms. Such batchwise reactions render the efficiency of utilizing enzymes or microorganisms very low. Recently, therefore, extensive studies have been made on immobilized enzymes or immobilized microorganisms which can be repeatedly or continuously used for the reaction by rendering enzymes water-insoluble while maintaining their activity or by molding microorganisms into an easy-to-recover size while also retaining their viability.

So far, various reports have appeared on processes for preparing immobilized enzymes or immobilized microorganisms. These processes are roughly divided into (a) an immobilizing process which comprises carrying enzymes or microorganisms on organic or inorganic water-insoluble substances by such means as covalent bonding, ionic bonding, or adsorption; (b) an immobilizing process which comprises covalently-bonding enzymes or microorganisms to one another with bifunctional reagents or the like; and (c) an immobilizing process which comprises entrapping enzymes or microorganisms in water-insoluble high-molecular weight substances hereinafter to be referred to as "entrapping process". Known examples of the entrapping process include a process which comprises dissolving a water-soluble monomer (such as acrylamide, vinylpyrrolidone, hydroxyethyl acrylate, or an acrylic acid salt), a water-soluble high-molecular weight substances (such as polyvinyl alcohol or polyacrylamide), or a water-soluble crosslinking agent (such as N, N'-methylenebis((acrylamide))) in water together with enzymes or microorganisms, and then causing the polymerization by the use of polymerization catalysts such as potassium persulfate or by use of radiation such as gamma rays. This process simultaneously imparts a crosslinked structure thereby including the enzymes or microorganisms in the resulting water-insoluble high-molecular weight gel. Another entrapping process is one which comprises dispersing an aqueous solution containing enzymes or microorganisms as fine droplets in an organic solvent having a water-insoluble monomer dissolved therein, and then initiating the polymerization. This encloses the fine water droplets in the resulting water-insoluble polymer. Still a third prior art process comprises dispersing an enzyme—or microorganism—containing aqueous solution as fine water droplets in an organic solvent having a water-insoluble high-molecular weight substance dissolved therein, and then removing the organic solvent to enclose the fine water droplets in the water-insoluble high-molecular weight substance.

Generally, enzymes or microorganisms are relatively stable in water but are unstable in organic solvents, and therefore, the materials frequently used in the conventional entrapping process are soluble in water. The use of water-soluble materials requires a procedure for making them water-insoluble by such means as polymerization or cross-linking, but this procedure inevitably entails the deterioration of the enzymes or microorganisms. The use of water-insoluble high-molecular weight substances as the entrapping materials, on the other hand, requires the use of organic solvents to dissolve them, with the result that the enzymes or microorganisms are deteriorated by the organic solvents.

SUMMARY OF THE INVENTION

It is therefore an object of the invention to provide a process for the preparation of immobilized enzymes or microorganisms.

Another object of the invention is to provide a process for immobilization of enzymes or microorganisms which does not extensively deactivate the enzymes or microorganisms.

Yet another object of the invention is to provide a process as mentioned above which will allow the production of said enzymes or microorganisms in the form of beads, powder, fibers, rods or films.

Still a further object of the invention is to provide a process mentioned above which will allow the preparation of entrapped enzymes or microorganisms.

These and other objects of the invention as hereinafter will become more readily apparent can be obtained by providing a process for preparing immobilized enzymes or microorganisms, which comprises dispersing cakes of ice containing enzymes or a microorganisms in an organic solvent having a water-insoluble high-molecular weight substance dissolved therein, removing the organic solvent from the ice cakes and thereafter entrapping said cakes or lumps in a high-molecular weight substance.

DESCRIPTION OF THE PREFERRED EMBODIMENTS

We have discovered that if the enzymes or microorganisms have been entrapped in an ice mass before immobilization they can be maintained in a stable condition for a long period of time, even when they are handled in an organic solvent and this ice mass can then be easily entrapped in a high-molecular weight substance. These discoveries have led us to the present invention.

The present invention, therefore, deals with a process for preparing immobilized enzymes or microorganisms which comprises dispersing ice lumps containing enzymes or microorganisms in an organic solvent having a water-insoluble substance dissolved therein, and then removing the organic solvent thereby entrapping said ice lumps in the water-insoluble high-molecular weight substance.

The enzymes used in the present invention may be those obtained from animal and plant tissues or those produced by microorganisms. The enzymes may be in purified or unpurified form, like for example, homogenates of enzyme-containing tissues or cells of microorganisms. The particular enzymes employed in the present invention are not critical to the invention. But they include, for example, oxido-reductases such as alcohol dehydrogenase, glucose oxidase, catalase, cholesterol oxidase, or uricase; transferases such as aspartate transcarbamylase, hexokinase, or ribonuclease; hydrolases such as α-amylase, β-amylase, gluco amylase, β-galactosidase, invertase, lipase, urease, pepsin, trysin, chymotrypsin, aminoacylase, or penicillin amidase; eliminating enzymes such as aspartic decarboxylase, aldolase, citric lyase, fumarase, or aspartase; isomerases such as glucose isomerase, or glutamate racemase; and synthetases such as aspartic synthetase, or glutathione synthetase.

The microorganisms used in the present invention are classified into moulds, yeasts, bacteria, ray fungi, and Fungi Imperfecti, but their type is not critical.

The microorganisms include, for example, the genus Aspergillus such as *A. niger, A. oryzae, A. terreus, A. itaconicus, A. flavus;* the genus Penicillum such as *P. chrysogenum, P. janthinellum, P. purpurogenum;* the genus Mucor such as *M. rouxii, M. mandshuricus;* the genus Rhizopus such as *R. nigricans, R. japonicus;* the genus Monascus such as *M. major, M. anka, M. rubiginosus;* the genus Saccharomyces such as *S. cerevisiae, S. rouxii, S. ludwigii;* the genus Schizosaccharomyces such as *S. pombe;* the genus Hansenula such as *H. miso;* the genus Pichia such as *P. membranaefacieus, P. glabrate;* the genus Candida such as *C. utilis;* the genus Pseudomonas such as *P. ovalis, P. stutzeri, P. dentrificans, P. aeruginosa, P. gravolens, P. fluorescens;* the genus Escherichia such as *E. coli;* the Aerobacter genus such as *A. aerogenes;* the genus Cornebacterium such as *C. glutamicus, C. acetophilum, C. hydrocarboclastus;* the genus Bacillus such as *B. subtilis, B. megaterium, B. brevis, B. coagulans, B. licheniformis;* the genus Brevibacterium such as *B. flavum, B. thiogentitales;* the genus Microbacterium such as *M. ammoniaphilum;* the genus Serratia such as *S. marcescens;* the genus Alcaligenes such as *A. marshallii;* the genus Acetobacter such as *A. aceti; A. melanogenum, A. suboxydans;* the genus Nitrosomonas such as *N. europaea, N. monocella;* the genus Nitrosococcus such as *N. nitrosus;* the genus Nitrosopia such as *N. breviensis, N. antarctica;* the genus Nitrosocystis such as *N. javanesis;* the genus Thiobaccillus such as *T. dentrificans;* the genus Lactobacillus such as *L. bulgaricus, L. casei, L. brevis, L. arabinosus, L. homohiochi, L. delbruckii;* the genus Streptomyces such as *S. olivochromogenus, S. kitazawaensis, S. archidaceus, S. garyphalus, S. lavendulae, S. roseochromogenus, S. griseus, S. bikiniensis, S. mashuensis, S. ruber, S. albus, S. antibioticus, S fradiae, S. erythraeus, S. alboniger, S. chrysomallus, S. noursei, S. hachijoensis, S. venezuelae. S. phaeochromogenus var chloromyceticus, S. thioluteus, S. celluflavus;* and the genus Fusarium such as *F. lini.*

According to the present invention, the microorganisms are grown in culture media, and are then used in a living condition. The living condition means that the microorganisms have a self-regenerating ability, and whether they are in living condition or not is confirmed by making the microorganisms present in an environment suited to the growth of the microorganisms. The environment suited to the growth of the microorganisms depends upon the respective microorganisms to be used, and is determined experimentally.

The ice masses or lumps containing enzymes or microorganisms used in the present invention refer to lumps of ice including enzymes or microorganisms inside them that have been formed by freezing an aqueous solution containing the enzymes or microorganisms in a deep-cooled atmosphere. The deep-cooled atmosphere may be a cooled gas or liquid, preferably, a liquid cooling medium that has been cooled. The liquid cooling medium is selected from liquid substances having a solidifying point of not higher than 0° C.

Examples of the liquid substances include methanol, ethanol, acetone, ethyl acetate, methylene dichloride, chloroform, carbon tetrachloride, ethyl ether, tetrahydrofuran, toluene, n-hexane, petroleum ether, liquid nitrogen, and liquid oxygen. They are cooled by a method which comprises utilizing the heat of vaporization or by means of an external coolant such as dry ice or the like, thereby cooling them directly. Another suitable method comprises cooling them indirectly by means of a refrigerator or the like.

When the liquid cooling medium is used to freeze an aqueous solution containing enzyme or microorganisms, the aqueous solution may be place in a container or the like for indirect freezing, or may be put in the liquid cooling medium for direct freezing. When it is directly frozen in the cooling medium, it is desirable to make the cooling temperature of the cooling medium as low as possible and further convert the aqueous solution into tiny water droplets by means of an atomizer or the like for quick freezing, in order to minimize the deactivation of the enzymes or the death of the microorganisms. The enzymes or microorganisms once included in the lumps of ice are stable even when allowed to stand in various organic solvents at a temperature lower than that of the melting point of ice.

In the present invention, moreover, various substances which are to be present mutually with enzymes or microorganisms can be used to protect the enzymes or microorganisms. Their examples include water-soluble high-molecular weight substances such as polyvinyl alcohol, polyethylene glycol, polyvinyl pyrrolidone, polyacrylamide, polyacrylic acid salts, polyethyleneimine, carboxymethyl cellulose, proteins, nucleic acids, or polysaccharides; polyhydric alcohols such as glycerin, or ethylene glycol; organic polar solvents such as dimethyl sulfoxide, dimethylformamide, dimethylacetamide, or dioxane; oligosaccharides such as sucrose, lactose, or maltose; amino acids such as glutamic acid, or aspartic acid; organic acids such as α-ketoglutaric acid, or malic acid; and metal salts such as salts of magnesium, manganese, cabalt, or calcium. Any of these substances can be included in lumps of ice together with enzymes or microorganisms by first adding them to an aqueous solution containing the enzymes or microorganisms, and then freezing the aqueous solution quickly in a cooled atmosphere.

The water-insoluble high-molecular weight substance useful in the present invention is a polymer which is soluble in an organic solvent but insoluble in water. Any of the water-insoluble high-molecular weight polymers which dissolve even slightly in an organic solvent at a temperature of not higher than 0° C. can be used in the present invention. Preferred, however, is a water-insoluble high-molecular weight substance which dissolves in an amount of about 0.1% by weight or more in an organic solvent at a temperature of not higher than 0° C. The fact that the water-insoluble high-molecular weight substance dissolves in an organic solvent means that the water-insoluble high-molecular weight substance mixes homogeneously with the organic solvent at a concentration in which no phase separation occurs between them.

The water-insoluble high-molecular substance used in the present invention is typified by homopolymers such as polyacrylonitrile, polyacrylic ester, polymethacrylic ester, polystyrene, polyvinyl acetate, polyvinyl chloride, or polycarbonate; or copolymers comprising the monomers constituting these homopolymers; or cellulose derivatives such as cellulose acetate, or ethyl cellulose. Any other water-insoluble high-molecular substance can also be used.

An organic solvent which dissolves the above water-insoluble high-molecular weight substances in an amount of 0.1% by weight or more at a temperature of not higher than 0° C. is selected from those present in liquid form at a temperature of not higher than 0° C. For instance suitable examples include methanol, ethanol, propanol, acetone, methyl ethyl ketone, ethyl acetate, methylene dichloride, chloroform, carbon tetrachloride, di-ethyl ether, toluene, xylene, n-hexane, petroleum ether, tetrahydrofuran, cyclohexane, N, N'-dimethylformamide, $\gamma$-butyrolactone, and acetonitrile, but the usable examples are not restricted thereto. The water-insoluble high-molecular weight substance is dissolved in such organic solvent, and then used while being cooled to a temperature of not higher than 0° C.

The organic solvent is removed and the lumps of ice containing the enzymes or microorganisms are thereby entrapped in the water-insoluble high-molecular weight substance. The procedure comprises dispersing the lumps of ice in a suspended state in an organic solvent which has the water-insoluble high-molecular weight substance dissolved therein at a temperature of not higher than 0° C. and then, removing the organic solvent thereby precipitating the water-insoluble high-molecular weight substance around the lumps of ice and entrapping the lumps of ice in the water-insoluble high-molecular weight substance. When the lumps of ice containing the enzymes or microorganisms are to be dispersed in an organic solvent having the water-insoluble high-molecular weight substance dissolved therein, a step may be added which comprises dissolving the water-insoluble high-molecular weight substance in an organic solvent, and then adding the lumps of ice which have been separately prepared followed by quick stirring, thus dispersing the ice lumps in a suspended state. Alternatively, a step may be added which comprises directly dispersing an enzyme—or microorganism—containing aqueous solution as tiny water droplets in the organic solvent which is being cooled and which has the water-insoluble high-molecular weight substance dissolved therein, thereby quickly freezing the dispersion to form ice masses containing the enzymes or microorganisms. To disperse the ice masses homogeneously in the organic solvent, it is preferred to use the ice masses having a diameter of not larger than 1 mm, because the smaller the particle size of the ice masses, the greater the effect is.

In order to maintain the once dispersed ice lump in the organic solvent in the stable state, a suitable amount of a non-solvent for the water-insoluble high-molecular substance may be added together with the ice lumps when they are dispersed. Particularly when the specific gravity of the ice lumps differs from the specific gravity of the organic solvent having the water-insoluble high-molecular substance dissolved therein, the once dispersed ice lumps are separated from the organic solvent if the stirring is stopped. To avoid this situation, a non-solvent may be added whereby the ice lumps can be dispersed stably in the organic solvent. The addition of a non-solvent for the water-insoluble high-molecular substance together with the ice lumps refers to the fact that the ice lumps are once slurried in a non-solvent for the water-insoluble high-molecular substance, whereafter the slurry is added with quick stirring to the organic solvent having the water-insoluble high-molecular substance dissolved therein. In this case, the ice lumps are dispersed, together with the non-solvent, in the organic solvent having the water-insoluble high-molecular substance dissolved therein. Therefore, the water-insoluble high-molecular substance is coagulated around the ice lumps, and the state is reached in which the coagulated water-insoluble high-molecular substance is half dissolved in the excess organic solvent. As a result, the ice lumps can be dispersed stably in the organic solvent having the water-insoluble high-molecular substance dissolved therein. To perform this procedure more effectively, it is also possible to include in the ice lumps a water-soluble high-molecular weight substance such as polyvinyl alcohol or polyethylene glycol, or a polyhydric alcohol such as glycerin or ethylene glycol. The non-solvent used to increase the dispersibility of the ice lumps is selected from those solvents which do not dissolve the water-insoluble high-molecular weight substance, which are liquid at a temperature of not higher than 0° C., and which are miscible with the organic solvent having the water-insoluble high-molecular weight substance dissolved therein.

To obtain the entrapped ice lumps from the water-insoluble high-molecular weight substance solution having the ice lumps dispersed therein, the solvent may be evaporated under reduced pressure, or there may be employed a method such as coagulating the water-insoluble high-molecular weight substance.

The enzymes or microorganisms are stable while being entrapped in the ice lumps even in the presence of the organic solvent. When the ice melts, however, the organic solvent is likely to cause the deactivation of the enzymes or the extinction of the microorganisms. It is therefore preferred to remove the organic solvent from the entrapping substance before the ice lumps melt. The removal of the organic solvent is performed by a method such as evaporation under reduced pressure.

The entrapped ice lumps from which the organic solvent has been removed are frozen for preservation, and are caused to melt before use, thereafter they can be used as immobilized enzymes or immobilized microorganisms. The entrapped lumps can be further freeze-dried by sublimation of the ice to assume a shape convenient for preservation and transportation. Freeze drying is carried out by using a vacuum freeze drying device.

The present invention provides an entirely novel process for preparing immobilized enzymes or microorganisms which involves entrapping enzymes or microorganisms in lumps of ice to prevent the deactivation of the enzymes or the death of the microorganisms which would otherwise be caused by an organic solvent, and entrapping the enzymes or microorganisms in a water-insoluble high-molecular weight substance in an organic solvent. Since prior art methods do not accomplish such entrapping of enzymes or microorganisms while rendering them stable in an organic solvent, the conventional methods cause various defects discussed supra. The drawbacks of the conventional methods can be eliminated by the present invention. The present invention also makes it possible to use various water-insoluble high-molecular weight substances now in wide use on a commercial scale and to prepare immobilized enzymes having stable enzymatic activity or immobilized microorganisms with the microorganisms entrapped in a viable condition. Furthermore, the immobilized enzymes or immobilized microorganisms produced by the present invention can be obtained in the form of beads, powder, fibers, rods, films, etc., and can be widely used as catalysts in producing various useful chemical substances. They can also be used for treating waste water or as means for analysis. Further, in the case of the immobilized microorganisms, in which the microorganisms are entrapped in a viable condition, they can be applied to reactions while made to effect self-regeneration by using them in a culture media.

Having generally described this invention, a further understanding can be obtained by reference to certain specific examples which are herein for purposes of illustration only and are not intended to be construed as limiting unless otherwise specified.

EXAMPLE 1

Mould gluco amylase (crude product made by Nagase Company, Ltd.) was suspended in demineralized water, and insolubles were then separated on a filter paper, thereby preparing a filtrate having a protein content of 32 mg/ml. Glycerin was dissolved in an amount of 5.0% by weight in the filtrate, and the solution was sprayed as tiny droplets into n-hexane at −75° C. which had been cooled with dry ice. Thereby the droplets were quickly frozen to form tiny lumps of ice containing gluco amylase. The ice lumps were promptly separated by suction-filtration over a Buchner funnel, and about 55 g of the ice lumps were slurried in 70 ml of a solvent mixture of n-hexane and methylene dichloride (mixing ratio: n-hexane/methylene dichloride=2/1 (vol/vol), cooled to −50° C.). The slurry was gradually added, with vigorous stirring, to 1,000 g of −15° C. methylene dichloride having 1.0% by weight of cellulose triacetate (a product of Mitsubishi Acetate Co., Ltd.) dissolved therein, whereby the ice lumps were dispersed. The dispersion was allowed to settle as liquid droplets onto a toluene bath cooled to −50° C., thereby coagulating the cellulose triacetate. The organic solvents, such as toluene, impregnated in the coagulated matter were removed under reduced pressure, and the residue was subsequently freeze-dried for a whole day to obtain particles of cellulose triacetate having gluco amylase entrapped therein.

The particles were classified, and 1.0 g of particles having a diameter of 0.5 to 1.0 mm were washed with an M/10 acetic acid buffer solution (pH 4.5) for a night with deaeration under reduced pressure. Then, 150 ml of an M/10 acetic acid buffer solution (pH 4.5) containing 5.0 wt.% of maltose was added, and the mixture was shaken at 40° C. for hydrolysis of the maltose. Glucose, hydrolysis product, contained in the reaction mixture was determined with Glucostat Reagent (a commercially available product of Fujisawa Medical Supply Co., Ltd.), whereby it was found that 2710 mg of glucose was formed after 1 hour of the reaction. The entrapped glucoamylase exhibited 19.8% of the activity recovery ratio with respect to unentrapped glucoamylase.

EXAMPLE 2

Coagulated matter was prepared in the same way as in Example 1. Toluene impregnated on the coagulated matter was removed by extraction with petroleum ether cooled to −50° C., and then, petroleum ether was removed by evaporation under reduced pressure, thereby obtaining coagulated matter of cellulose triacetate having ice lumps entrapped therein. The coagulated matter was allowed to stand in a refrigerator maintained at about 5° C. to melt the ice lumps thereby obtaining particles having gluco amylase-containing tiny water droplets entrapped therein.

The particles were subjected to classification to give particles having a diameter of 0.5 to 1.0 mm. These particles (1.0 g; dry weight 0.15 g) were washed and measured for activity in the same way as in Example 1. It was found thereby that 746 mg of glucose was formed upon 1 hour reaction. The entrapped gluco amylase exhibited 32.7% of the activity recovery ratio with respect to the unentrapped gluco amylase.

EXAMPLE 3

Gluco amylase-containing ice lumps prepared in the same way as in Example 1 were dispersed in methylene dichloride having cellulose triacetate dissolved therein, in the same manner as in Example 1. The dispersion was cast in the form of a thin film on a cooled glass sheet. Then, the methylene dichloride was gradually evaporated under reduced pressure, whereafter the film was freeze-dried overnight, thereby to obtain a cellulose triacetate film having gluco amylase entrapped therein. The film was finely cut to a size of 0.5 mm square, and 0.5 g of the cut product was washed in the same way as in Example 1. Measurement of its activity in the same way as in Example 1 showed that 978 mg of glucose was formed upon 1-hour reaction. Calculation of the entrapped gluco amylase exhibited 15.7% of the activity recovery ratio with respect to the unentrapped gluco amylase.

EXAMPLES 4, 5, 6 and 7

The procedure of Example 2 was repeated using, instead of gluco amylase used in Example 1, each of invertase (a commercially available product of Wako Junyaku Kabushiki Kaisha), catalase (a commercially available product of Seikagaku Kogyo Kabushiki Kaisha), β-galactosidase (a commercially available product of Funakoshi Pharmaceuticals Co., Ltd.) and urease (a commercially available product of Seikagaku Kogyo Kabushiki Kaisha). Thereby was obtained particulate cellulose triacetate having each of invertase, catalase, β-galactosidase and urease entrapped therein. This particulate product was subjected to classification to give a particulate substance having a diameter of 0.5 to 1.0 mm. 1.0 Grams (wet weight) of the particulate substance was washed with demineralized water, and the washed substance was measured for its activity by the method described below.

Invertase:

The entrapped invertase after washing was put in 150 ml of an M/10 acetic acid buffer solution (pH 4.5) containing 5.0% by weight of sucrose, followed by reaction at 40° C. for 1.0 hour under shake. The resulting glucose was determined with Glucostat reagent. One unit was set at an amount enough to exhibit activity to decompose 1μ mole of sucrose per minute at 40° C. at a pH of 4.5.

Gatalase:

The entrapped catalase after washing was put in 100 ml of an M/20 phosphoric acid buffer solution (pH 7.0) containing 40 m Mol of $H_2O_2$, and the reaction was performed at 25° C. The decomposition rate of $H_2O_2$ was determined by measuring the decreasing rate of the absorbance at 240 m$\mu$ by means of an ultraviolet spectrophotometer every two minutes. One unit was set at an amount enough to exhibit activity to decompose $H_2O_2$ in an amount of 1$\mu$ mole per minute at 25° C. at a pH of 7.0.

$\beta$-Galactosidase:

The entrapped $\beta$-galactosidase after washing was put in 150 ml of an M/10 phosphoric acid buffer solution (pH 5.2) containing 5.0% by weight of lactose, and the solution was shaken at 40° C. for 1 hour for reaction. The resulting glucose was determined with Glucostat reagent. One unit was set at an amount in which to show activity for decomposing 1$\mu$ mole of lactose per minute at 40° C. at a pH of 5.2.

Urease:

The entrapped urease after washing was placed in 100 ml of an M/2 phosphoric acid buffer solution (pH 7.0) containing 3.0% by weight of urea, and the reaction was performed for 10 minutes at 25° C. The resultant ammonia was determined with a Nessler reagent. One unit was set at an amount to show activity for decomposing 1$\mu$ mole of urea per minute at 25° C. at a pH of 7.0.

The following table shows the activity per gram (dry weight) of the invertase, catalase, $\beta$-galactosidase and urease each entrapped in cellulose triacetate, as well as the activity recovery-ratio of the entrapped enzyme with respect to the activity of the unentrapped enzyme.

| Ex. No. | Entrapped Enzyme | Activity (U/g) | Activity Recovery Ratio (%) |
|---|---|---|---|
| 4 | Invertase | 310.7 | 35.9 |
| 5 | Catalase | 710.0 | 25.0 |
| 6 | $\beta$-Galactosidase | 159.2 | 30.2 |
| 7 | Urease | 169.3 | 29.0 |

EXAMPLE 8

About 30 g of ice lumps containing gluco amylase that had been prepared in the same way as in Example 1 were slurried in 50 ml of a solvent mixture of n-hexane and methylene dichloride (mixing ratio: n-hexane/methylene dichloride=$\frac{1}{2}$ (vol./vol.), cooled to $-50°$ C.). The slurry was added slowly, with rapid stirring, to 400 g of methylene dichloride ($-10°$ C.) having 2.5% by weight of methyl polymethacrylate dissolved therein, thereby to disperse the ice lumps. The dispersion was allowed to fall as droplets into n-hexane cooled to $-50°$ C., thereby coagulating the methyl polymethacrylate. The organic solvents impregnated to the coagulated matter were removed under reduced pressure, and subsequently, freeze-drying was carried out for a whole day to obtain methylpolymethacrylate particles having gluco amylase entrapped therein. The particles were classified to give particles having a particle size of 0.5 to 1.0 mm. 1.0 Gram of the particles were washed in the same way as in Example 1, and the activity was measured in the same way as in Example 1. It was found that 712 mg of glucose was formed upon the reaction performed for 1 hour. The entrapped gluco amylase exhibited 9.5% of the activity recovery ratio with respect to the unentrapped gluco amylase.

EXAMPLE 9

About 30 g of gluco amylase-containing ice lumps prepared in the same manner as in Example 1 were slurried in 50 ml of a solvent mixture of N,N'-dimethylformamide and methanol (mixing ratio: N,N'-dimethylformamide/methanol=4/1 (vol./vol.), cooled to $-45°$ C.). The slurry was added gradually, with quick stirring, to 700 g of N,N'-dimethylformamide ($-10°$ C.) having 1.0% by weight of a copolymer of acrylonitrile with vinyl acetate (weight ratio: acrylonitrile/vinyl acetate=91/9) dissolved therein, thereby to disperse the lumps. Then, the dispersion was cast in the form of a thin film on a glass sheet kept in the cooled condition, and then, dipped in a methanol bath cooled to $-60°$ C. to coagulate the copolymer. The organic solvents included in the copolymer were removed under reduced pressure, and subsequently, the copolymer was freeze-dried for a whole day, to obtain a film-like copolymer having gluco amylase entrapped therein. The film-like copolymer was finely cut to 0.5 mm squares, and the cut product (1.0 g) was washed in demineralized water for one night with deaeration under reduced pressure. Then, the activity was measured in the same manner as in Example 1. As a result, it was found that 1420 mg of glucose was formed after 1-hour reaction. The entrapped gluco amylase exhibited 18.7% of the activity recovery ratio of the unentrapped gluco amylase.

EXAMPLE 10

The procedure of Example 9 was repeated except that invertase was used instead of the gluco amylase and a copolymer of acrylonitrile and styrene (weight ratio: acrylonitrile/styrene=29/71) was used instead of the copolymer of acrylonitrile and vinyl acetate. Thereby was obtained a copolymer film having invertase entrapped therein. The film was finely cut to 0.5 mm square, and 1.0 g of the cut product was washed overnight in demineralized water with deaeration under reduced pressure. Then, the activity was measured by the same measuring method as in Example 4. It was found, as a result, that 1871 mg of glucose was formed by 1-hour reaction. Thus, the entrapped invertase showed an activity recovery ratio of 15.1% with respect to the activity of unentrapped invertase.

EXAMPLE 11

Corynebacterium glutamicum was inoculated to a culture medium (initial pH 7.0) containing 4.5% by weight of glucose, 0.5% by weight of urea, 0.5% by weight of $(NH_4)_2SO_4$, 0.1% by weight of yeast extract, 0.05% by weight of $KH_2PO_4$, 0.05% by weight of $K_2HPO_4$, 0.025% by weight of $MgSO_4.7H_2O$, 0.001% by weight of $FeSO_4.7H_2O$, 0.0008% by weight of $MnSO_4.H_2O$, 10$\mu$ liter/liter culture medium of biotin, and 25 drops/liter culture medium of soybean oil, and cultured at 30° C., for 24 hours under shake. To the culture solution were added 5.0% by weight of glycerin, 3.0% by weight of sucrose, and 1.0% by weight of sodium L-glutamate. The mixture was sprayed as tiny droplets into n-hexane cooled to $-75°$ C. with dry ice for quick freezing, thereby forming ice lumps containing Corynebacterium glutamicum. The ice lumps were promptly recovered by a Buchner funnel, and then, about 30 g of the ice lumps were slurried in 50 ml of a solvent mixture of n-hexane and methylene dichloride (mixing ratio: n-hexane/methylene dichloride=1/1 (vol./vol.), cooled to $-50°$ C.). The slurry was added slowly, with quick stirring to 500 g of methylene dichloride (−10° C.) having 0.5% by weight of methyl polymethacrylate and 1.5% by weight of cellulose triacetate dissolved therein, thereby dispersing the ice lumps. Then, the dispersion was caused to settle as liquid droplets into an n-hexane bath cooled to −50° C., thereby to obtain a coagulated substance.

The organic solvents included in the coagulated substance were removed under reduced pressure, and the residue was freeze-dried for a whole day to give a particulate dry substance having *Corynebacterium glutamicum* entrapped therein. That *Corynebacterium glutamicum* entrapped in the dry substance was living immediately after the freeze-drying and even after being allowed to stand in vacuo for about 1 month at 10° C. was confirmed by the method described below.

1.0 Gram of the dry substance was cut finely by means of a cutter, and suspended in 100 ml of sterile water. The suspension was shaken for about 30 minutes at a temperature of 10° C. to release the cells. 1 Milliliter of the cell solution was poured into 10 ml of the aforementioned culture medium that had been sterilized. Then, culture was proformed under shake, with the result that microbial growth was observed in both of the cases in which the microbe was contained in the dry substance immediately after freeze-drying and in which it was contained in the dry substance allowed to stand in vacuum at 10° C. for about 1 month after the freeze-drying. The grown microbe was compared microscopically with unentrapped *Corynebacterium glutamicum*, whereby the grown microbe was identified to be *Corynebacterium glutamicum*. These facts helped confirm that *Corynebacterium glutamicum* entrapped in the dry substance was in a viable condition.

EXAMPLE 12

A culture medium (initial pH 7.0) containing 10% by weight of glucose, 0.5% by weight of urea, 0.1% by weight of $K_2HPO_4$, 0.05% by weight of $MgSO_4.7H_2O$, 2% by weight of $CaCO_3$, and 0.7% by weight of corn steep liquor (CSL) was inoculated with *Serratia marcescens*, which was cultured for 24 hours at 30° C. under shaking. After incorporating therein 5.0% by weight of glycerin, 1.0% by weight of polyethylene glycol, 2.0% by weight of dextran, and 0.5% by weight of sodium L-glutamate, the culture solution was sprayed as tiny drops into n-hexane cooled to −75° C. with dry ice, to freeze the drops quickly. Thus were formed ice lumps containing *Serratia marcescens*. About 30 g of the ice lumps were slurried in a solvent mixture of n-hexane and methylene dichloride as in Example 11, and the slurry was added gradually, with quick stirring, to 500 g of methylene dichloride (−10° C.) having 0.5% by weight of polycarbonate and 1.5% by weight of cellulose triacetate dissolved therein, thereby dispersing the ice lumps. Then, the dispersion was dropped as droplets into an n-hexane bath cooled to −50° C., thereby to obtain a coagulated substance. The organic solvents included in the coagulated substance were removed under reduced pressure, followed by freeze-drying the residue for a whole day, to obtain a particulate dry substance having *Serratia marcescens* entrapped therein.

Confirmation of the viability of *Serratia marcescens* entrapped in the dry substance was made in the same way as in Example 11. As a result, it was confirmed that *Serratia marcescens* entrapped in the dry substance was in a viable condition.

EXAMPLE 13

A culture medium (initial pH 7.0) containing 1.0% by weight of meat extract, 1.0% by weight of peptone, 0.25% by weight of glucose and 0.5% by weight of NaCl was inoculated with *Escherichia coli*, which was cultured at 30° C. for 24 hours under shake. After incorporating therein 5.0% by weight of glucose, 5.0% by weight of serum albumin, 3.0% by weight of polyethylene glycol and 4.0% by weight of glycerin, the culture solution was sprayed as tiny droplets into −75° C. n-hexane cooled with dry ice for quick freezing. Thus were formed ice lumps containing *Escherichia coli*. About 10 g of the ice lumps were dispersed in 100 ml of N,N′-dimethylformamide (−10° C.) having 1.5% by weight of a copolymer of acrylonitrile with vinyl acetate (weight ratio: acrylonitrile/vinyl acetate=91/9) dissolved therein, and the dispersion was cast on a glass sheet that was cooled. The glass sheet with the cast dispersion was further cooled to a temperature in the vicinity of −50° C. and then dipped in a methanol bath having a temperature of −50° C. thereby coagulating the copolymer. The organic solvents impregnated to the coagulated copolymer were removed under reduced pressure, followed by freeze-drying the residue for a whole day, to obtain a film-like copolymer having *Escherichia coli* entrapped therein.

The viability of *Escherichia coli* entrapped in the film-like copolymer was checked in the same manner as in Example 11, whereby it was confirmed that *Escherichia coli* entrapped in the film-like copolymer was in a viable condition.

EXAMPLE 14

A culture medium (initial pH 6.0) containing 0.35% by weight of peptone, 0.3% by weight of yeast extract, 0.3% by weight of malt extract, 1.0% by weight of glucose, 0.2% by weight of $KH_2PO_4$, 0.1% by weight of $(NH_4)_2SO_4$, and 0.01% by weight of $MgSO_4.7H_2O$ was inoculated with *Saccharomyces cerevisiae*, which was cultured at 30° C. for 48 hours under shake. In the culture solution were incorporated 5.0% by weight of glycerin, 3.0% by weight of peptone and 2.0% by weight of dimethyl sulfoxide, whereafter ice lumps containing *Saccharomyces cerevisiae* were formed in the same ways as in Example 11. About 30 g of the ice lumps was slurried in 50 ml of a solvent mixture of n-hexane and methylene dichloride (mixing ratio: n-hexane/methylene dichloride=1/1 (vol. vol.), cooled to −50° C.). The slurry was added gradually, with quick stirring, to 500 g of methylene dichloride (−10° C.) having 2.5% by weight of cellulose triacetate dissolved therein, to disperse the ice lumps. Then, the dispersion was dropped as droplets into a toluene bath cooled to −50° C., thereby obtaining coagulated particles of cellulose triacetate. The organic solvents impregnated to the coagulated particles were removed under reduced pressure, and subsequently, the residue was freeze-dried for a whole day to give dry particles of cellulose triacetate having *Saccharomyces cerevisiae* entrapped therein. Confirmation of viability of *Saccharomyces cerevisiae* entrapped in the dry particles was checked in the same manner as in Example 11.

EXAMPLE 15

*Penicillum chrysogenum* was implanted in a culture medium (initial pH 5.5) containing 2.0% by weight of lactose, 1.0% by weight of glucose, 6.0% by weight of corn steep liquor (CSL), 0.3% by weight of $NaNO_3$, 0.05% by weight of $KH_2PO_4$, 0.0125% by weight of $MgSO_4.7H_2O$, and 0.5% by weight of $CaCO_3$, and cultured at 25° C. for 3 days. In the culture solution were incorporated 5.0% by weight of glycerin, 5.0% by weight of sodium L-glutamate and 3.0% by weight of honey, and then, ice lumps containing *Penicillum chrysogenum* were formed in the same way as in Example 11. About 10 g of the ice lumps were dispersed in N,N'-dimethylformamide having a copolymer of acrylonitrile with vinyl acetate dissolved therein, followed by coagulating the copolymer in methanol, in the same way as in Example 13. The organic solvents included in the coagulated copolymer were removed under reduced pressure, and the residue was freeze-dried for a whole day, thereby obtaining a copolymer film having *Pencillum chrysogenum* entrapped therein.

Viability of *Penicillum chrysogenum* entrapped in the film was checked in the same manner as in Example 11, and it was thus confirmed that *Penicillum chrysogenum* entrapped in the dry product was in a viable condition.

EXAMPLE 16

*Streptomyces griseus* was implanted in a culture medium (initial pH 7.0) containing 0.5% by weight of glucose, 0.5% by weight of soluble starch, 0.05% by weight of L-asparagine 0.05% by weight of $K_2HPO_4$, 0.05% by weight of $MgSO_4.7H_2O$, 0.05% by weight of KCl, 0.001% by weight of $FeSO_4.7H_2O$, and 0.05% by weight of yeast extract, where the fungus was cultured at 27° C. for 48 hours under shake. In the culture solution were incorporated 5.0% by weight of glycerin, 5.0% by weight of serum albumin and 1.0% by weight of polyethylene glycol, and ice lumps containing *Streptomyces griseus* were formed in the same way as in Example 11. About 30 g of the ice lumps were dispersed in methylene dichloride having cellulose triacetate dissolved therein, in the same way as in Example 14, and the cellulose triacetate was coagulated in toluene as in Example 14. The organic solvents incorporated in the coagulated substance were removed under reduced pressure, followed by freeze-drying the residue for a whole day, to obtain dry particles of cellulose triacetate having *Streptomyces griseus* entrapped therein.

Viability of *Streptomyces griseus* entrapped in the dry particles was checked in the same way as Example 11, thereby containing that *Streptomyces griseus* entrapped in the dry particles was in a viable condition.

Having now fully described this invention, it will be apparent to one of the ordinary skill in the art, that many changes and modifications can be made thereto without departing from the spirit or scope of the invention set forth herein.

What is claimed as new and intended to be covered by Letters Patent is:

1. A process for preparing immobilized enzymes or microorganisms, which comprises dispersing lumps of ice containing an enzyme or a microorganism in an organic solvent having a water-insoluble high-molecular weight substance dissolved therein, at a temperature not higher than 0° C. wherein the organic solvent dissolves at least 0.1% by weight of the water-insoluble high-molecular weight substance at a temperature of 0° C. or lower, and the removing the organic solvent thereby entrapping the ice lumps in the water-insoluble high-molecular weight substance.

2. The process of claim 1 wherein the organic solvent having the water-insoluble high molecular weight substance dissolved therein is removed under reduced pressure.

3. The process of claim 1 wherein the organic solvent having the water-insoluble high-molecular weight substance dissolved therein is removed with the use of a non-solvent for the water-insoluble high-molecular weight substance.

4. The process of any of claims 1, 2 or 3 wherein the lumps of ice containing the enzyme or microorganism are formed by freezing an aqueous solution containing the enzyme or microorganism in cooling medium.

5. The process of claim 4 wherein the cooling medium is a liquid substance having a solidifying point of 0° C. or lower.

6. The process of claim 1 wherein the lumps of ice containing the enzyme or microorganism have a diameter of at most 1 mm.

7. The process of claim 1 wherein the water-insoluble high-molecular weight substance is a cellulose acetate or an ethyl cellulose.

8. The process of claim 1 wherein the water-insoluble high-molecular weight substance is selected from the group consisting of polyacrylonitrile, polyacrylic ester, polymethacrylic ester, polystyrene, polyvinyl acetate, polyvinyl chloride, polycarbonate, and a copolymer consisting of the monomers constituting these homopolymers.

* * * * *